(12) United States Patent
Waterman

(10) Patent No.: US 6,358,519 B1
(45) Date of Patent: Mar. 19, 2002

(54) GERM-RESISTANT COMMUNICATION AND DATA TRANSFER/ENTRY PRODUCTS

(76) Inventor: Ruth S. Waterman, 5201 S. Liberty St., New Orleans, LA (US) 70115

( * ) Notice: Subject to any disclaimer, the term of this patent is extended or adjusted under 35 U.S.C. 154(b) by 0 days.

(21) Appl. No.: 09/249,053

(22) Filed: Feb. 12, 1999

Related U.S. Application Data

(60) Provisional application No. 60/074,795, filed on Feb. 16, 1998.

(51) Int. Cl.[7] ..................... A01N 25/34; A01N 25/00; A01N 25/08; H04M 1/17
(52) U.S. Cl. ................. 424/404; 424/405; 424/409; 379/381; 379/439; 379/370
(58) Field of Search ................... 424/404, 405, 424/78.24, 78.35, 445, 402, 409, 411; 428/441

(56) References Cited

U.S. PATENT DOCUMENTS 5,238,749 A  *  8/1993  Cueman et al. ............. 424/441
5,882,667 A  *  3/1999  Jones ......................... 424/405

FOREIGN PATENT DOCUMENTS

JP           406104966    *  4/1994   ................. 379/439

* cited by examiner

Primary Examiner—Thurman K. Page
Assistant Examiner—Blessing Fubara
(74) Attorney, Agent, or Firm—LaRiviere, Grubman & Payne, LLP

(57) ABSTRACT

Articles and a method related to use of a biocide (e.g., triclosan) incorporated into communication and data transfer/entry products in order to provide cleaner, fresher and more hygienic surfaces by controlling a broad range of gram-positive and gram-negative bacteria, yeast, and fungi on the surfaces of such products.

15 Claims, 2 Drawing Sheets

GERM-RESISTANT COMMUNICATION AND DATA TRANSFER/ENTRY PRODUCTS

CROSS-REFERENCE TO RELATED APPLICATIONS

This application claims priority to U.S. provisional patent application No. 60/074,795 of the same title and inventorship as this application, and being filed on Feb. 16, 1998. U.S. Provisional Patent application Ser. No. 60/074,795, is hereby incorporated by reference in its entirety.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a form of infection control among the various populations that use various communication and data transfer/entry products. More particularly, the present invention relates to an antimicrobial protection that is incorporated into all types of plastics of which communication and data transfer/entry products are composed, thus providing deterrence to the growth of bacteria, molds and fungi.

2. General Background

Germs are everywhere. These tiny microbes, such as bacteria, fungi and mold can be found on most every communication and data transfer/entry product. Although many of the microbes are harmless, others can cause illness. These illnesses can be spread from one person to another through contact with the contaminated surface. Most people who come in contact with the contaminated surfaces would simply experience a bout with a cold or have symptoms of a stomach virus, but for the very young or those with weakened immune systems, such an illness can have life-threatening results. Implementing the usage of communication and data transfer/entry products of the present invention, which are protected with antimicrobial agents in hospitals and other institutions would decrease their role as possible vectors for the transmission of diseases.

Another factor is that antibiotic usage, in general, has increased significantly in the past years. This has led to current problems of resistance among bacterial pathogens to commonly prescribed antibiotics because of inappropriate prescribing (1,2). At the same time, transactions around the world have become quicker, and travel has become more commonplace and accessible to the general population. This is due, largely, to the increase in economic development and world-wide urbanization. This leads to the fact that the general population has become more dependent upon communication and data transfer/entry products. In fact, the majority of the population comes into contact with communication and/or data transfer/entry products on a daily basis. Those who do not are quickly learning to overcome their functional illiteracy.

The majority of communication and data transfer/entry product are constructed of various types of plastic. These plastics possess minute empty spaces where microbes are able to proliferate. Many of the microbes growing on these plastic products possess the ability to cause infection and contamination. Of particular concern are products which are exposed to many different environments, such as digital pagers and cell phones, and those products which have multi-users: public pay phones, keyboards at multi-user computers. Introducing an antimicrobial agent into the manufacturing process of communication products would lead to the decrease of microbial proliferation on such products, possibly diminishing the amount of community acquired and nosocomial infections.

Already various articles that incorporate antimicrobial agents into their manufacturing process are being marketed. Some of these products include: chopping boards, cloths, clothing (wet suits, exercise tights), kitchen implements, food containers, children's toys and highchairs, surgical incision drapes, dental instrument trays, acrylic and cellulose acetate fiber productions, pillows, mattress pads, pillow ticking and mops.

It is felt that there is a necessity for the protection of communication and data transfer/entry products by incorporating antimicrobial agents, since there is currently no evidence of such products. Moreover, the possibility that these devices could be vectors in the transmission of infectious diseases also points to the value of such an invention.

SUMMARY OF THE INVENTION

The invention is the encompassing of everyday communication products with the idea of infection control. More particularly, the invention is focused on decreasing the number of pathogens available to cause community acquired infections. The invention relates to communication and data transfer/entry products which include at least one antimicrobial agent in their surfaces, in order to reduce transmission of infectious agents.

There are three steps that are required for the transmission of an infectious agent to an uninfected person. Firstly, the pathogen must be excreted by the infected person from the nose, mouth or feces. Second, the pathogen must be transferred to the well person. This transfer could be through the air, via direct contact or by way of an intermediary surface. Finally, the infectious agent must reach a susceptible site in the uninfected person (3). This invention would be particularly useful in deterring the transfer of pathogens via intermediary surfaces that had been contaminated by infected people. And, communication and data entry products are continually in contact with hands, and near mouths and eyes, all of which are susceptible sites for an infectious agent to proliferate.

Health care facilities including hospitals, extended-care facilities, sub-acute care facilities, skilled nursing facilities, nursing homes, assisted living centers and rehabilitation centers represent sites where those requiring medical care and those providing medical care converge. Specifically, hospitals, in large measure, are sites where acute medical care is delivered by trained health care personnel. It is well recognized that the above mentioned sites harbor microorganisms that possess markedly greater virulence. Infections resulting from these microorganisms have an increased threat of causing morbidity and mortality. The issue of nosocomial (institution acquired) infections, their cost in terms of total lives and money, and their prevention and control has been receiving increased attention on both a national and global level (4,5). Moreover, the ability of microorganisms to reproduce, mutate and generate resistance to current antibacterial therapy has been accepted as a rapidly developing world-wide hazard (2, 6–8). The "gap" between the generation of resistant microbes and the production of new and potentially efficacious antimicrobial drugs has been increasing at an alarming rate. This "gap" has been the topic of recent medical articles (4,6,7).

Despite infection control guidelines and policies including those issued by the National Centers for Disease Control and Prevention (CDC), the "gap" has continued to grow. One contributing factor to this growth is the fact that people act a vectors for infection transmission due to the devices and equipment with which they come into contact. Because of this, novel approaches to infection control and prevention must be explored and advocated (8). The introduction of this invention into medical facilities will aid in the diminishment of the transfer of pathogens by the fact that there will be fewer microorganisms available.

Antimicrobial agents, such as chlorinated phenoxy and polyhexamethylene beguanidide hydrochlorides, which incorporable into plastics suitable for use with communication and data transfer/entry products, are known to suppress the growth of Staphylococcus which is important since Staphylococcus can cause many diseases in humans: boils, carbuncles, folliculitis, impetigo, contagiosa, osteomyelitis, endocarditis, meningitis, enteritis, enterotoxin, nephritis, pharyngitis, laryngitis, bronchitis, pneumonia and cellulitis. Staphylococci are members of a group of invasive gram-positive bacteria known as the pyogenic (pus-producing) cocci. Staphylococci, harbored by either an asymptomatic carrier or a person with the disease, can be spread by the hands, expulsion from the respiratory tract, and transport in or on animate and inanimate objects. Staphylococci can produce disease in almost every organ and tissue of the body. Moreover, resistant strains of staphylococci may originate in the community as well as in the hospital (9). Because of these facts, it is important to limit the proliferation of this microbe. In addition, the emergence of vancomycin-resistant *Staphylococcus aureus* (VRSA), which is difficult to treat, makes the control of this bacteria even more important. Two cases of VRSA have been reported in the United States as well as one in Japan (2). The VRSA strains of bacteria have the potential to become a public health hazard that could lead to high rate of mortality; therefore, whatever can be done to circumvent these microbes would be to the population's benefit. The population at large should be aware of naively spreading germs and infections to one another—this invention would cut down on the number of germs available for spreading.

Handwashing, originally advocated by Semmelweiss in the nineteenth century, is know to reduce the spread and transfer of microorganisms. Certainly, it is an important aspect of infection control. However, what good does a hand washing do if after a person has washed their hands, they immediately return to the use of a communication or data transfer/entry product that is infested with microbes? A recent public health notice from the FDA stated that "improper handling of devices between uses can contaminate facilities and expose individuals . . . to infectious, biohazardous material" (10). This is evidence for the need for products that come into contact with numerous people to be protected from the proliferation of infectious microbes. For, in the instant invention, products including antimicrobial agents in their surfaces would alleviate some of the contamination that occurs when devices are improperly handled between uses.

In a preferred embodiment, the active antimicrobial component may be a chemical called triclosan (also known as Irgasan DP300, discussed in more detail below). Triclosan becomes equilibrated in a plastic matrix because its molecules are able to migrate within it. Some will, therefore, reach the surface forming an equilibrium between the surface and internal triclosan. The triclosan is able to kill microorganisms, or at least inhibit their growth. Removal of the triclosan from the surface, by cleaning, disrupts the equilibrium in the matrix. As a result, more of the triclosan molecules migrate slowly to the surface and restore the balance. This process takes about 30 minutes. As the amount of the triclosan on the surface represents a small proportion of the whole, the useful life of the product as an inhibitor is very long. The triclosan material has been tested against mold, fungus, *E. coli*, salmonella, listeria, klebsiella, staphylococcus and streptococcus.

The largest advantage of the present invention is the fact that there would be communication products with decreased microbial capacity available to all consumers. This could lead to the reduction of community acquired and nosocomial infections. The current invention would also give consumers peace of mind; they would know that the product they bought prevents the multiplication of infection causing microbes. In addition, the protection lasts the life-time of the product, giving the consumer assurance of the defense of the inventive product. Furthermore, this invention can be incorporated into all forms of communication and data transfer/entry products that are made of plastics and/or fabrics.

Another advantage of the present invention is that it has the potential to decrease health care costs. If community acquired and nosocomial infections decrease, there will be fewer days spent in the hospital, at clinics and away from work. In addition, the constant uprising of resistant microbes would be on the decline, for there would be fewer places for them to proliferate, and, thus, fewer areas for such microbes to infect the general population.

These and other aspects of the present invention will become apparent to those of ordinary skill in the art by reference to the following description and to the appended drawings.

DETAILED DESCRIPTION OF THE INVENTION

Figure 1:
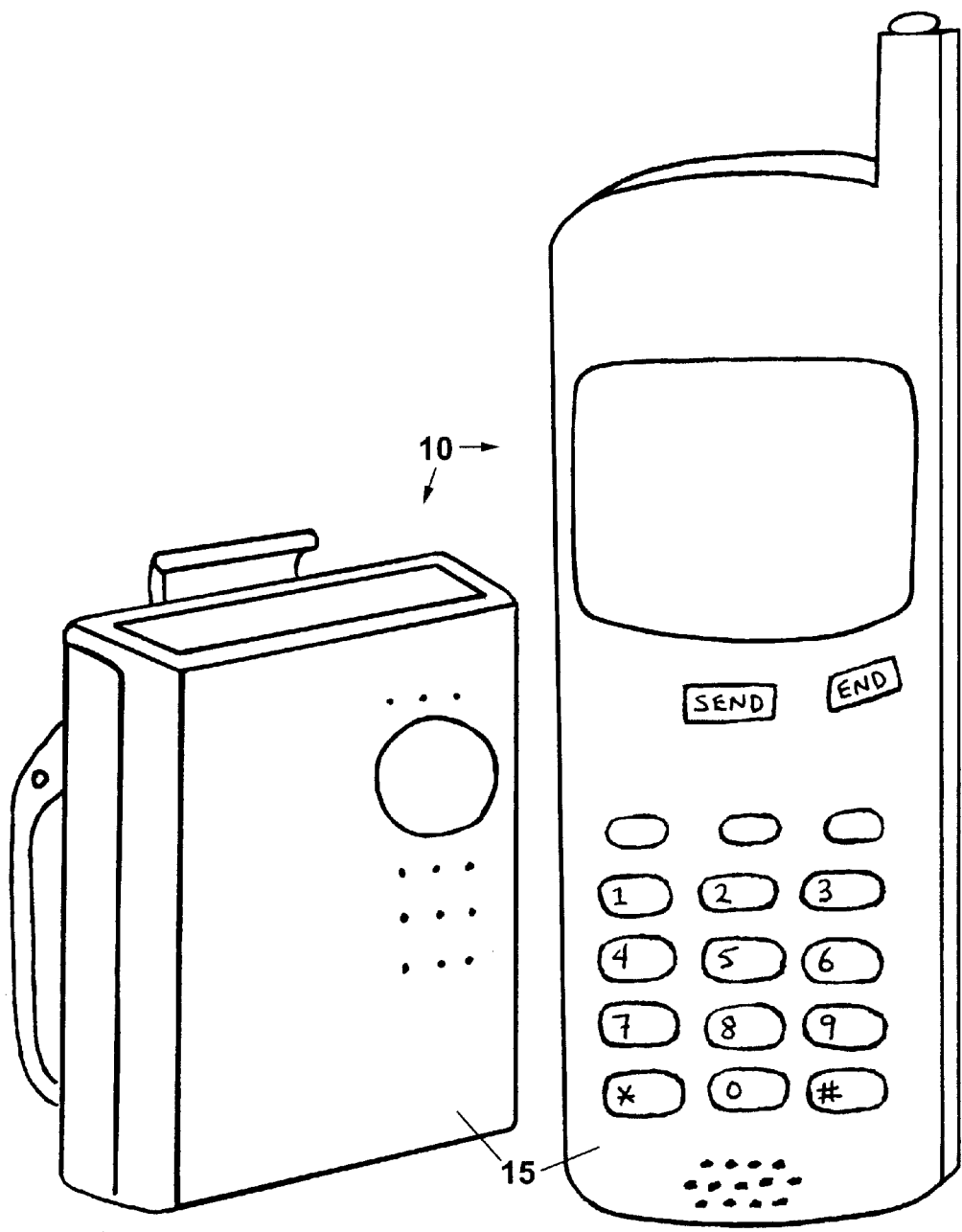
FIG. 1 shows views of various data processing products and/or devices of the present invention.

The present invention relates to surfaces of data processing products, including communication and data transfer/data entry devices, containing a suitable amount of an antimicrobial agent, such as triclosan, such that growth of microorganisms is inhibited on such surfaces thereby promoting asepsis on such surfaces.

It is to be understood that the terms "data processing product" and "date processing device" as used herein include communication and data transfer/data entry devices such as, but not limited to the following, which are provided merely as illustrative examples and are in no way intended to limit the scope of the present invention, a) those with a limited number of users, but with prolonged exposure, including but not limited to, pagers (including digital pagers), private telephones (including digital and cellular), personal computer keyboards and related devices (including computer "mice"), watches, pens and other writing instruments, remote controls (for example, for stereos, televisions, car alarms, garage doors, and so forth), security system components (including key pads and remote controls), credit, check and debit cards, audiovisual keypads and buttons (including television and radio keypads), musical instruments, including keyboards, bar code readers, calculators, fax machines, electronic lock key pads and the like; b) those with multiple users and prolonged exposure, including but not limited to, office and public telephones, computer keyboards, electronic game keyboard and buttons, pens and other writing devices, remote controls including those for audiovisual equipment and security systems, cash register keypads, calculators, fax machines, audiovisual keypads and buttons, copy machine keypads, bar code readers, electronic lock keypads, gambling machine handles and buttons, and the like; and c) those with many users with brief exposure, including for example but not limited to, public and office telephones, computer keyboards, pens and other writing devices, automated teller machine keypads, elevator controls, petroleum delivery (e.g., gas pump) controls, electronic lock keypads, security system keypads, copy machine keypads and the like (note several products overlap depending upon the nature of their use and no category is exclusive or limiting in any way).

Each data processing product of the present invention has at least one surface which comes into contact with a human being. Such surface is composed of a polymeric material, such as a plastic.

In the present invention, an antimicrobial agent is associated with the data processing product, particularly with the surface of the product, wherein the antimicrobial agent is provided as a topical applicant applied to the surface, or incorporated into the polymeric material thereof, wherein the antimicrobial agent is selected from the group consisting of, for example, chlorinated phenoxy and polyhexamethylene biguanidide hydrochloride (including triclosan (Irgansan DP3000) sold under the trade name MICROBAN®), and wherein when the antimicrobial agent is incorporated into the polymeric material of the surface, the antimicrobial agent exhibits controlled migration through the polymeric material to the exposed surface thereof wherein an imbalance of vapor pressure of the antimicrobial agent demands equalization to thereby continuously inhibit growth of microorganisms and promote asepsis on the surface of the data processing product.

It is to be understood that the products of the instant invention will inhibit the growth of a broad range of microorganisms on their surfaces because of the incorporated antimicrobial agent in the surface. Examples of diseases which can be inhibited by the antimicrobial effect of the present surface of the data processing products include, but are not limited to the following infectious diseases which can be transmitted though indirect contact or via droplets: bacteremia, conjunctivitis, *clostridium difficile* infection, cutaneous and pharyngeal diphtheria, enterococcus, *escherichia coli* 0157:H7, *haemophilus influenza,* herpes simplex, meningitis, mucocutaneous, mumps, *mycoplasma pneumoniae,* pertussis, pharyngitis, gastroenteritis, rubella (congenital), scabies, shigellosis, smallpox, staphylococcal infection, pneumonia (lung abscess), streptococcal infection, varicella, vibrio infection.

Further, the present invention relates to a method of manufacturing data products and/or devices which have a surface having antimicrobial characteristics that inhibit microorganism growth and promote asepsis on the surface, which method comprises, for example: providing a data processing device or product having at least one surface which comes into contact with the user of the product or device, the surface comprising a polymeric material such as a plastic, associating an antimicrobial agent with the surface by applying the antimicrobial agent to the surface as a topical applicant to the surface or by incorporating the antimicrobial agent into the polymeric material of the surface, selecting the antimicrobial agent from the group consisting of a chlorinated phenoxy and polyhexamethylene biguanidine hydrochloride, wherein when the antimicrobial agent is incorporated into the polymeric material of the surface, the antimicrobial agent exhibits controlled migration though the polymeric material comprising the surface when an imbalance of vapor pressure of the antimicrobial agent demands equalization thereby continuously inhibiting microorganism growth and promoting asepsis on the surface.

Referring to the drawing, FIG. 1 shows various data processing devices and products 10 of the present invention, each having at least one surface, 15, which comes into contact with a user of the product or device. In each instance, the surface 15 of the data processing product or device 10 contains a broad spectrum antimicrobial agent in sufficient quantity to inhibit the growth of microorganisms on the surface and promote asepsis on the surface. The surface may be composed of a polymeric material formed in an injection molding or other molding process.

In a preferred embodiment, the surface 15 is fabricated by injection molding or other molding process of a polymeric material such as polyethylene. The particular polymeric material used to manufacture the surface 15 is determined in accordance with the characteristics desired to suit a particular working environment and use.

In a preferred embodiment, the antimicrobial agent is incorporated into the polymeric material from which the surface 15 is made from. Thus, there is incorporated therein an effective amount of an antimicrobial biocidal or biostatic substance, such as a chlorinated phenoxy. In a preferred embodiment, the antimicrobial agent incorporated therein is resistant to growth of fungus, yeast, viruses, and Gram-positive and Gram-negative bacteria including Staph, *E. coli,* Klebsiella and Salmonella. Antimicrobial agents include, for example, PHMD, triclosan, Irgansan DP300, MICROBAN® products, chlorinated phenoxy 5-cholor-2-(2,4-dichlorophenoxy) phenol, polyhexamethlyene biguanidie hydrochloride, CH3635, Ster-zac, 5-Cholro-2-(2,4-dichlorophenoxy)phenol, Cholro-2-)2,4-dichloror)phenol, Chloro-2-(2,4-dichlorophenoxy) phenol, Lexol 300, Trhciloro-2-hydroxydiphenyl ether, and for example, including all those antimicrobial agents described in the following U.S. patents, which are hereby incorporated by reference in their entirety: U.S. Pat. Nos. 5,586,643, 5,288, 480, 4,098,877, 5,069,907 and 238,749. Many of these compounds are sold by the Microban Products Company, Huntsville, N.C. Other suitable chemical components having known antimicrobial biocidal or biostatic characteristics may also be used in the present invention.

The preferred method of associating the antimicrobial agent with the surface 15 is to incorporate it into the synthetic polymeric master batch prior to forming the surface 15. In that respect, the antimicrobial agent in powder form may be added as a component of the mixture comprising the synthetic polymeric material and preferably comprises from between about 0.05 percent to about 2.0 percent, by weight, of the mixture. More preferably, the antimicrobial biocidal or biostatic agent is from between about 0.1 percent to about 1.0 percent, by weight, of the synthetic polymer into which it is incorporated. The resulting synthetic polymeric admixture is injection molded or formed by another molding process to provide the surface 15 of the data processing product 10.

In use the antimicrobial agent migrates through the polymeric material to the exposed surface thereof from the amorphous zones of the polymer until equilibrium of the antimicrobial agent's internal vapor pressure is reached. If the antimicrobial substance of the surface 15 is removed by friction or other means, more antimicrobial agent will move to the surface until the agent's internal vapor pressure is once again at equilibrium.

Alternatively, the antimicrobial agent can be associated with the surface 15 by spraying a topical applicant thereon, or by running the surface 15 through a bath comprising the antimicrobial agent.

All measurements disclosed herein are at standard temperature and pressure, at sea level on Earth, unless indicated otherwise. All materials used or intended to be used in a human being are biocompatible, unless indicated otherwise.

EXAMPLE

To lend support to the necessity of such an invention, two separate studies were commissioned, both of which were performed by ASTM certified microbiologists.

The first study analyzed the bacterial flora on the following data transfer/entry products: public telephones, pagers (of health care workers and non-health care workers), cellular phones, computer keyboards, and telephones in a health care setting. The total number of products evaluated totaled 30. A sample was gathered from each product using replicate organism detection and culturing (RODAC) plates. The bacterial flora was analyzed by culturing these plates to determine the total aerobic bacterial load and appropriate tests were run to determine if any pathogenic and/or resistant organisms had been found.

Out of the 30 products that were cultured, 26 (86.7%) of them grew out of at least one pathogenic bacteria.

The number of samples that were collected in each category of data transfer/entry products is listed below:

| | |
|---|---|
| Public Telephone | 7 |
| Pager (non-health care worker) | 5 |
| Cellular phone | 5 |
| Pager (health care worker) | 6 |
| Computer keyboard (health care setting) | 4 |
| Telephone (health care setting) | 3 |
| Total | 30 |

The itemization of pathogens that grew on each sample is listed in Table 1.

TABLE 1

PAGER (HEALTH CARE WORKER)

1. *STAPHYLOCOCCUS AUREUS*
2. *ENTEROBACTER AGGLOMERANS*
3. COAGULASE-NEGATIVE STAPHYLOCOCCUS
4. COAGULASE-NEGATIVE STAPHYLOCOCCUS
5. COAGULASE-NEGATIVE STAPHYLOCOCCUS
6. COAGULASE-NEGATIVE STAPHYLOCOCCUS, ENTEROCOCCUS SSP.

COMPUTER KEYBOARD (HEALTH CARE SETTING)

1. NO GROWTH
2. *ENTEROBACTER AGGLOMERANS, STAPHYLOCOCCUS AUREUS*
3. COAGULASE-NEGATIVE STAPHYLOCOCCUS

TABLE 1-continued

4. ENTEROBACTER AGGLOMERANS, METHICILLIN-RESISTANT *STAPHYLOCOCCUS AUREUS*

TELEPHONE (HEALTH CARE)

1. COAGULASE-NEGATIVE STAPHYLOCOCCUS
2. METHICILLIN-RESISTANT *STAPHYLOCOCCUS AUREUS*
3. COAGULASE-NEGATIVE STAPHYLOCOCCUS

PUBLIC TELEPHONE

1. *STAPHYLOCOCCUS AUREUS*
2. NO GROWTH
3. *ENTEROBACTER AGGLOMERANS*
4. COAGULASE-NEGATIVE STAPHYLOCOCCUS, ENTEROCOCCUS SSP.
5. *STAPHYLOCOCCUS AUREUS*
6. METHICILLIN-RESISTANT COAGULASE-NEGATIVE STAPHYLOCOCCUS
7. NO GROWTH

PAGER (NON-HEALTH CARE WORKER)

1. STAPHYLOCOCCUS AUREUS
2. METHICILLIN-RESISTANT COAGULASE-NEGATIVE STAPHYLOCOCCUS, ENTEROCOCCUS SSP.
3. METHICILLIN-RESISTANT COAGULASE-NEGATIVE STAPHYLOCOCCUS
4. COAGULASE-NEGATIVE STAPHYLOCOCCUS
5. COAGULASE-NEGATIVE STAPHYLOCOCCUS

CELLULAR PHONE

1. *STAPRYLOCOCCUS AUREUS*
2. COAGULASE-NEGATIVE STAPHYLOCOCCUS
3. COAGULASE-NEGATIVE STAPHYLOCOCCUS
4. NO GROWTH
5. COAGULASE-NEGATIVE STAPHYLOCOCCUS

Figure 2:
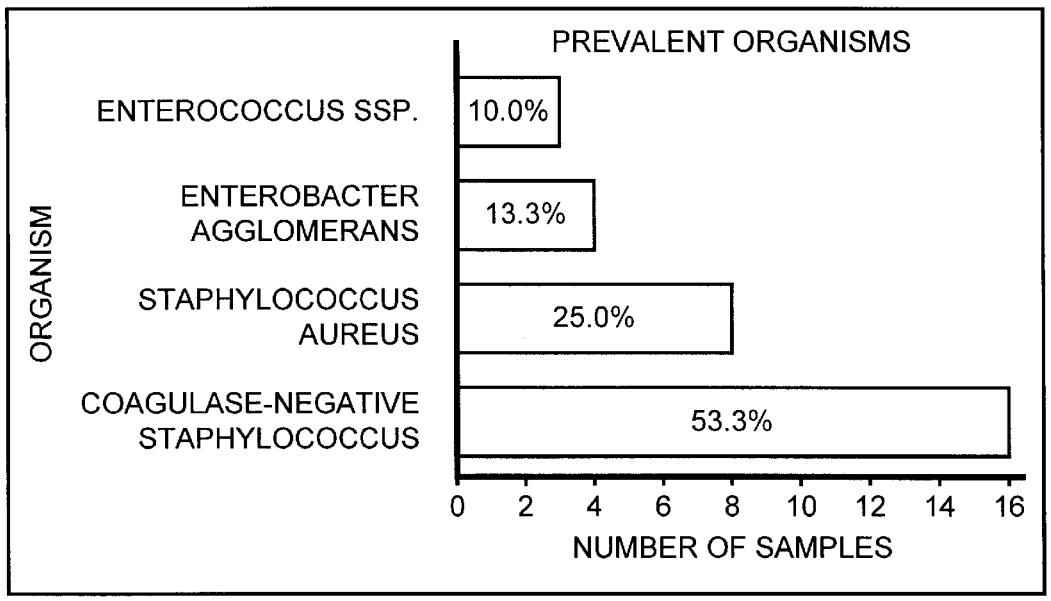
FIG. 2 shows the prevalence of different types of pathogens on sample products.

The prevalence of the four types of pathogens that were recovered from the study is shown in FIG. 2. Coagulase-negative staphylococcus was found on 16 (53.3%) of the sampled products. Three of the 16 (18.8%) coagulase-negative staphylococcus were methicillin resistant. *Staphylococcus aureus* was the second most prevalent with 8 (26.7%) of the cultures growing it. Of the 8 *staphyloccus aureus* specimens, 2 (25%) were methicillin resistant. Enterobacter agglomerans was found on 4 (13.3%) of the products and enterococcus SSP were found on 3 (10%).

In the second study, which consisted of 50 samples, only pagers were cultured. The samples were divided into two groups—health care workers and non-health care workers. The samples were gathered by swabbing each pager with a culturette. The culturettes were then transferred to the appropriate plates and allowed to incubate. After incubation, the plates were examined for bacterial flora. Specific tests were employed to evaluate pathogenicity and resistance.

Figure 3:
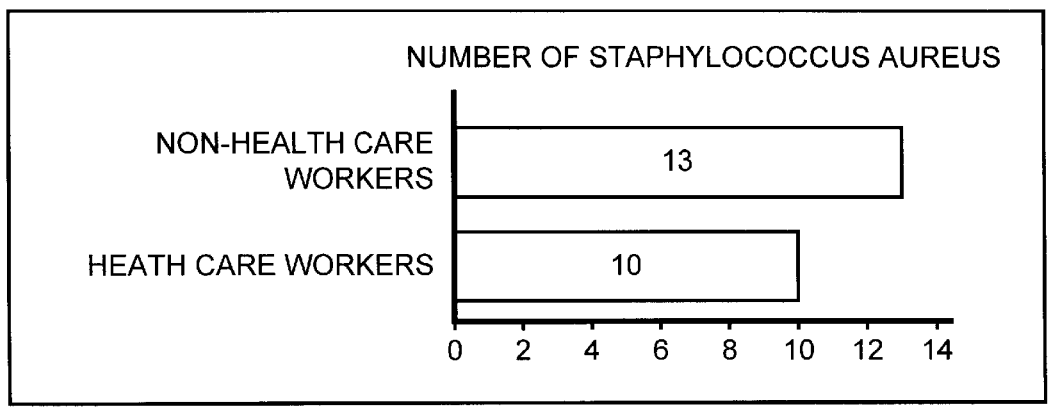
FIG. 3 shows the prevalence of pathogens related to health care workers.

Of the 50 samples, 42 (84%) grew one or more potentially pathogenic bacteria. 26 (52%) of the samples tested were from health care workers, while the remaining 24 (48%) were from non-health care workers. 22 (84.6%) of the 26 samples from the health care workers grew out potential pathogens, while 20 (83.3%) of the 24 samples from non-health care workers showed evidence of a potential pathogen. The most prevalent pathogen found in this study was *staphylococcus aureus*. 23 (54.7%) of the 42 pagers that carried potential pathogens grew out *staphylococcus aureus*. 10 (43.4%) of these samples were from healthcare workers, while 13 (56.6%) were from non-health care workers (see FIG. 3). A total of 3 (13%) of the *staphylococcus aureus* were methicillin-resistant. Two of the methicillin-resistant *staphylococcus aureus* were from the non-health care worker group, while 1 was from the health care worker group. The second most common potential pathogen found was coagulase-negative staphylococcus. 14 (33.3%) of the samples carried this type of bacteria. Diptheroids, a large group of gram-positive bacteria and also a potential pathogen, was found on 9 (21.4%) of the sampled pagers. Enterobacter agglomerans, enterococcus SSP., and burkholderia cepucia were each found on one sample, respectively.

According to a report from the National Nosocomial Infection Surveillance (NNIS) system, all of the microbes recovered from data transfer/entry articles in a health care setting during the first study were within the top six reported nosocomial pathogens (11).

Over the past 40 years, gram positive bacteria, such as *staphylococcus aureus* and enterococcus SSP, has become more of an important organism in hospital infections (12, 13). Enterococci are normal flora of the gastro-intestinal tract. Their resistance to antibacterials allows survival in an environment with high use of antibiotics. In addition, this organism can survive heat and dessication, enabling it to survive in the environment for prolonged periods of time. Wendt and colleagues found that some enterococcal strains can survive for greater than four months under dry conditions (14). Another recent report found that vancomycin-resistant enterococcus are capable of prolonged survival on hands, environmental surfaces and gloves (15).

*Staphylococcus aureus* is a major hospital and community acquired pathogen. These bacteria gain motility and accessibility to human beings on hands or clothes of hospital personnel (16, 17). In addition, community acquired methicillin-resistant *staphylococcus aureus* is on the rise (18).

Coagulase-negative staphylococcus is a leading cause of nosocomial infections. An estimated 60–90% of these strains are methicillin resistant, and there have been reports of vancomycin-resistant coagulase-negative staphylococcus (19–21).

In order to prevent the transmission of deadly and virulent pathogens, it is recommended that gloves are immediately removed after contact with an infected patient and hands are promptly and thoroughly washed. Difficulty arises in that health care workers cannot dispose of their pagers after seeing an infected patient. Therefore, they are destined to carry pathogens with them as they make their rounds.

The bacteria that were found on the data transfer/entry products that we sampled reinforce the need for the present invention. In addition, the fact that our studies show that data transfer/entry products have the capability of carrying resistant bacteria is even more of an alarm.

The factors that may increase antibacterial resistance in the hospital include: increased severity of the illnesses of hospitalized patients, more severely immunocompromised patients, ineffective infection control and isolation practices, increased use of antibacterial prophylaxis, increased emperic polymicrobial antimicrobial therapy, increased antimicrobial usage per geographic area per unit time, increased introduction of resistant organisms from the community and newer devices and procedures in use.

Of the above, those which are of specific interest are the last two. New devices in the hospital setting can certainly include cellular phones, pagers and computers. When these products are being used without the incorporation of infection control, then they negate their purpose. Mainly, the promotion and expediency of effective medicine. The increasing presence of resistant organisms arising in a community setting is also of concern. Our studies clearly show that there are resistant pathogens residing on data transfer/entry products. Products containing an antimicrobial component would assist in decreasing the amount of bacteria available for proliferation.

The economic implications of resistant bacterial infections are vast. Patients infected with a resistant pathogen require a disproportionate amount of health care stay and risk of mortality are greatly increased. There are over 2.1 million nosocomial infections annually in the United States. Because of this, hospitals lose between $583–$4886 per each infection (22). Pinner et al. found that the death rate in the United States due to infectious disease as the underlying cause of death increased 58% between 1980 and 1992 (23). Why, when patients requiring inpatient surgery is decreasing and those requiring outpatient is increasing are we finding more infections which end in death? The answer has to lie in infection control.

Today's infection control measures must include mechanisms to detect the various manners in which the infection occurs. Specifically, the ways in which a host can acquire a particular organism. The following hosts are especially at risk for infection: the immunocompromised, those with chronic cardiovascular disease, chronic vascular disease or diabetes cerebrospinal fluid leaks, persons with functional or anatomical asplenia (absence of the spleen), the immunocompetent (those over 65 years), anyone with human immunodeficiency virus (HIV), leukemia, lymphoma, Hodgkin's disease, multiple myeloma, chronic renal failure of nephrotic syndrome. Those receiving immunosuppresive chemotherapy, and those who have had an organ or bone marrow transplant. This list is vast and most people in industrialized nations daily come into contact with people who fall into at least one of the categories.

Perhaps much can be learned from Krilov and Associates' study which used the following intervention to decrease infections in a day care: attention to environmental cleaning and disinfection, with an emphasis on toys. They found a marked decrease in respiratory infections, a decrease in days missed and a trend towards a decrease in otitis media (ear infection) and sinusitis. In addition, total reported illnesses significantly decreased as did physician visits and antibiotic usage (24).

Adults have their special form of toys, and many of them can be encompassed in the category of data transfer/entry products. Providing these "toys" with an antimicrobial component may also lead to a significant decrease in the amount of illness society endures.

The foregoing embodiments are presented by way of example only; the scope of the present invention is to be limited only by the following claims.

REFERENCES

1. Craig, W. A., "The Future—Can We Learn From the Past?", *Diagnostic Microbiology and Infectious Disease,* 27(1–2):49–53 (1997).
2. Flores, P. A., Gordon, S. M., "Vancomycin-Resistant *Staphylococcus Aureus:* An Emerging Public Health Threat", *Cleveland Clinic Journal of Medicine,* 64(10) :527–531 (1997).
3. Donowitz, L. E., "Infection Control for the Health Care Worker", Williams and Wilkins, Baltimore, Md., 1995.
4. Amabile-Cuevas, C. F., Cardenas-Garcia, M., Ludgar, M., "Antibiotic Resistance", *American Scientist,* 83:320–329 (1995).
5. Neu, H. C., "The Problem of Bacterial Resistance", *Challenges in Infectious Diseases,* 1(1):1 (1993).
6. Anon., "Vancomycin Resistance Control Measures can be Effective", *ASM News,* 62(1):17–18 (1996).

7. Friedland, I. R., McCracken, Jr., G. H., "Management of Infections Caused by Antibiotic Resistant Streptococcus Pneumoniae", *Drug Therapy,* 331(6):377–382 (1994).
8. "Report of the ASM Task Force on Antibiotic Resistance", *Antimicrobial Agents and Chemotherapy,* (suppl):1–23 (1995).
9. Saravolatz, L. D., Pohlod, D. J., Arkiing, L. M., "Community-Acquired Methicillin-Resistant *Staphylococus Aureus* Infections: A New Source for Nosocomial Outbreaks", *Annals of Internal Medicine,* 97:325–329 (1982).
10. Public Notice from FDA's Center for Devices and Radiological Health, Apr. 17, 1997.
11. NNIS. Data Summary from October 1986–April 1996. 1–3; 1996.
12. Swartz, M. N., "Hospital-Acquired Infections:Diseases With Increasingly Limited Therapies. Proccedings of the National Academy of Sciences of the United States of America. 91(7):2420–7; 1994.
13. Neu, H. C. "Infection Problems for the 1990's-Do We Have an Answer?" *Scandinavian Journal of Infectious Disease.* Suppl. 91:7–13; 1993.
14. Wendt, C., Wiesenthal, B, Dietz, E., Ruden, H. "Survival of Vancomycin-Resistant and Vancomycin-Susceptible Enterococci on Dry Surfaces." *Journal of Clinical Microbiology.* 36(12):3734–36; 1986.
15. Noskin, G. A., Stoso, V., Cooper, I., Peterson, L. R. "Recovery of Vancomycin-Resistant Enterococci on Fingertips and Environmental Surfaces." *Infection Control and Hospital Epidemiology.* 16(10):577–81; 1995.
16. Boyce, J. M., Jackson, M. M., Pugliese, G., Batt, M. D., Fleming, D., Garner, J. J. et al. "Methicillin-Resistant *Staphylococcus Aureus* (MRSA): A Briefing for Acute Care and Hospital and Nursing Facilities." *Infection Control and Hospital Epidemiology.* 15:105–15:1994.
17. Speer, B. S., Shoemaker, N. B., Salyers, A. A. "Bacterial resistance to Tetracycline:Mechanisms, Transfer and Clinical Significance." *Clinical Microbiology Review.* 15:387–99; 1992.
18. Saravolatz, L. D., Pohlod, D. J., Arking, L. M. "Community-Acquired Methicillin-Resistant *Staphylococus Aureus* Infections: ANew Source of Nosocomial Outbreaks." *Annals of Internal Medicine.* 97:325–29; 1982.
19. Sanyal, D., Johnson, A. P., George, R. C., Edward, R., Greenwood, D. "In-vitro Characteristics of Glycopeptide Resistant Strains of Staphylococcus Epidermidis Isolated From Patients on CAPD." *Journal of Antimicrobial Chemotherapy.* 32–267–78; 1993.
20. Schwalbe, R. S., Stapleton, J. T., Gilligan, P. H. "Emergence of Vancomycin Resistance in Coagulase-Negative Staphylococcus." *New England Journal of Medicine.* 316:927–31; 1987.
21. Veach, L. A., Pfaller, M. A., Barrett, M., Koontz, F. P., Wenzel, R. P. "Vancomycin Resistance in Staphylococcus Haemolyticus Causing Colonization and Bloodstream Infection." *Journal of Clinical Microbiology.* 28:2064–68; 1990.
22. Jarvis, W. R. "Selected Aspects of the Socioeconomic Impact of Nosocomial Infections: Morbidity, Mortality, Cost and Prevention." *Infection Control and Hospital Epidemiology.* 17(8):552–57; 1996.
23. Pinner, R. W., Teutsch, S. M., Simonsen, L., Klug, L. A., Graber, J. M., Clarke, M. j., Berkelman, R. L. "Trends in Infectious Disease Mortality in the United States." *The Journal of the American Medical Association.* 275(3): 189–93; 1996.
24. Krilov, L. R., Barone, S. R., Mandel, F. S., Cusack, T. M., Gaber, D. J., Rubino, J. R. "Impact of an Infection Control Program in a Specialized Preschool." *American Journal of Infection Control.* 24(3):167–73; 1996.

What is claimed is:

1. A germ-resistant article for information communication or manipulation comprising:

a device for information communication or manipulation selected from the group consisting essentially of cellular and digital phones, digital pagers, personal digital assistant (PDA) devices, personal computer keyboards, personal computer mice, watches having information communication or manipulation function, dictation devices, portable note-taking devices, remote controls, security system key pads and remote controls, credit, check and debit cards having information-storage components, information-storage cards, smart cards, electronic signature cards, audiovisual keypads and buttons, musical keyboards, bar code readers, calculators, fax machines, electronic lock key pads, office and public telephones, electronic game keyboards and buttons, cash register keypads, copy machine keypads, gambling machine handles and buttons, automated teller machine keypads, elevator controls, and gas pump controls, utilizing the electromagnetic energy spectrum, and having a surface comprising a polymeric material; and at least one antimicrobial agent selected from the group consisting essentially of chlorinated phenoxy and poly-hexamethylene biguanide hydrochloride incorporated within the surface, wherein the antimicrobial agent exhibits controlled migration through the polymeric material of the surface when an imbalance of vapor pressure of the antimicrobial agent demands equalization, thereby continuously inhibiting microbial growth and promoting asepsis on the surface.

2. The germ-resistant article for information communication or manipulation of claim 1, wherein the antimicrobial agent is 5-chloro-2-(2,4-dichlorophenoxy)phenol.

3. The germ-resistant article for information communication or manipulation of claim 2, wherein the antimicrobial agent is present in the polymeric material of the surface in an amount of between about 0.05 percent to about 2.0 percent by weight.

4. The germ-resistant article for information communication or manipulation of claim 3, wherein the polymeric material of the surface is polyethylene.

5. A method of manufacturing a germ-resistant article for information communication or manipulation having at least one surface having antimicrobial characteristics that inhibit microbial growth and promote asepsis on the surface, comprising:

making an admixture of polymeric material and an antimicrobial agent selected from the group consisting of chlorinated phenoxy and poly-hexamethylene biguanide hydrochloride, forming a surface for a device for information communication or manipulation by molding said admixture of polymeric material and antimicrobial agent, wherein in the surface, the antimicrobial agent exhibits controlled migration through the polymeric material of the surface when an imbalance of vapor pressure of the antimicrobial agent demands equalization to thereby continuously inhibit microbial growth and promote asepsis on the surface.

6. The method of claim 5, wherein the chlorinated phenoxy is 5-chloro-2-(2,4-dichlorophenoxy)phenol.

7. The method of claim 5, wherein the antimicrobial agent is present in the polymeric material of the surface in an amount of between about 0.05 percent to about 2.0 percent by weight.

8. The method of claim 5, wherein the device for information communication or manipulation is selected from the group consisting of cellular and digital phones, digital pagers, personal digital assistant (PDA) devices, personal computer keyboards, personal computer mice, watches having information communication or manipulation function, dictation devices, portable note-taking devices, remote controls, security system key pads and remote controls, credit, check and debit cards having information-storage components, information-storage cards, smart cards, electronic signature cards, audiovisual keypads and buttons, musical keyboards, bar code readers, calculators, fax machines, electronic lock key pads, office and public telephones, electronic game keyboards and buttons, cash register keypads, copy machine keypads, gambling machine handles and buttons, automated teller machine keypads, elevator controls, and gas pump controls.

9. The method of clam 5, wherein the polymeric material of the surface is polyethylene.

10. A method of manufacturing a device for information communication or manipulation possessing at least one surface possessing antimicrobial characteristics that inhibit microbial growth and promote asepsis on the surface, which comprises:

providing a surface of a polymeric material for a device for information communication or manipulation;

associating an antimicrobial agent, selected from the group consisting of chlorinated phenoxy and polyhexamethylene, with said surface by applying said antimicrobial agent as a topical applicant to said surface;

thereby forming a polymeric surface containing the antimicrobial agent, wherein in the surface the antimicrobial agent exhibits controlled migration through the polymeric material of the surface when an imbalance of vapor pressure of the antimicrobial agent demands equalization, to thereby continuously inhibit microbial growth and promote asepsis on the surface.

11. The method of claim 10, wherein the chlorinated phenoxy is 5-chloro-2(2,4-dichlorophenoxy)phenol.

12. The method of claim 10, wherein the antimicrobial agent is present in the polymeric material of the surface in an amount of between about 0.05 percent to about 2.0 percent by weight.

13. The method of claim 10, wherein the device for information communication or manipulation is selected from the group consisting of cellular and digital phones, digital pagers, personal digital assistant (PDA) devices, personal computer keyboards, personal computer mice, watches having information communication or manipulation function, dictation devices, portable note-taking devices, remote controls, security system key pads and remote controls, credit, check and debit cards having information-storage components, information-storage cards, smart cards, electronic signature cards, audiovisual keypads and buttons, musical keyboards, bar code readers, calculators, fax machines, electronic lock key pads, office and public telephones, electronic game keyboards and buttons, cash register keypads, copy machine keypads, gambling machine handles and buttons, automated teller machine keypads, elevator controls, gas pump controls.

14. The method of claim 10, wherein the polymeric material of the surface is polyethylene.

15. The germ-resistant article for information communication or manipulation of claim 1 wherein the device for information communication or manipulation selected from the group consisting essentially of cellular and digital phones, digital pagers, personal digital assistant (PDA) devices, personal computer keyboards, personal computer mice, watches having information communication or manipulation function, dictation devices, portable note-taking devices, remote controls, security system key pads and remote controls, credit, check and debit cards having information-storage components, information-storage cards, smart cards, electronic signature cards, audiovisual keypads and buttons, musical keyboards, bar code readers, calculators, fax machines, electronic lock key pads, office and public telephones, electronic game keyboards and buttons, cash register keypads, copy machine keypads, gambling machine handles and buttons, automated teller machine keypads, elevator controls, and gas pump controls, utilizing the electromagnetic energy spectrum, and having a surface comprising a polymeric material, is a device that performs more than one information communication or manipulation function.

\* \* \* \* \*

UNITED STATES PATENT AND TRADEMARK OFFICE
CERTIFICATE OF CORRECTION

PATENT NO.   : 6,358,519 B1                                         Page 1 of 1
DATED        : March 19, 2002
INVENTOR(S)  : Ruth S. Waterman It is certified that error appears in the above-identified patent and that said Letters Patent is hereby corrected as shown below:

<u>Title page,</u>
Item [57] ABSTRACT, lines 2 and 3, delete "communication and data transfer/entry products" and replace with -- devices for information communication and manipulation --;

<u>Column 1,</u>
Lines 61 and 62, delete "Those who do not are quickly learning to overcome their functional illiteracy.";

<u>Column 3,</u>
Line 8, delete "a" and replace with -- as --;

<u>Column 4,</u>
Line 57, delete ""date" and replace with -- "data --;

<u>Column 6,</u>
Line 34, delete "from";
Lines 44-46, delete "5-Cholro-2-(2,4dichlorophenoxy)phenol, Cholro-2- )2,4-dichloror) phenol, Chloro-2-(2,4-dichlorophenoxy) phenol,"

<u>Column 8,</u>
Line 26, delete "STAPRYLOCOCCUS" and replace with -- STAPHYLOCOCCUS --;

<u>Column 13,</u>
Line 22, delete "clam" and replace with -- claim --;

Signed and Sealed this

Twenty-eighth Day of May, 2002

Attest:

JAMES E. ROGAN
*Attesting Officer*   *Director of the United States Patent and Trademark Office*